United States Patent [19]

Wallace

[11] Patent Number: 5,025,035

[45] Date of Patent: Jun. 18, 1991

[54] METHOD OF TREATING DEPRESSION

[75] Inventor: Jan D. Wallace, Ann Arbor, Mich.

[73] Assignee: Warner-Lambert Company, Morris Plains, N.J.

[21] Appl. No.: 596,270

[22] Filed: Oct. 12, 1990

[51] Int. Cl.[5] .................. A61K 31/20; A61K 31/205; A61K 31/215

[52] U.S. Cl. .................................. 514/530; 514/552; 514/559

[58] Field of Search ........................ 514/530, 552, 559

[56] References Cited

U.S. PATENT DOCUMENTS 4,024,175  5/1977  Satzinger et al. ................... 260/468
4,087,544  5/1978  Satzinger et al. ................... 424/305

*Primary Examiner*—Stanley J. Friedman
*Attorney, Agent, or Firm*—Elizabeth M. Anderson

[57] ABSTRACT

The instant invention is a novel use of known cyclic amino acids. Such compounds, including gabapentin, are useful for treating major and minor forms of depression.

3 Claims, No Drawings

METHOD OF TREATING DEPRESSION

BACKGROUND OF THE INVENTION

The present invention relates to a novel therapeutic use of a known compound, gabapentin, its derivatives, and pharmaceutically acceptable salts. The present invention concerns a method for treating depression in a mammal in need of such treatment.

U.S. Pat. No. 4,024,175 and its divisional 4,087,544 cover the compounds of the instant invention, methods for preparing them, and several uses thereof. The uses disclosed are: protective effect against cramp induced by thiosemicarbazide; protective action against cardiazole cramp; the cerebral diseases epilepsy, faintness attacks, hypokinesia, and cranial traumas; and improvement in cerebral functions. The compounds are useful in geriatric patients. The patents are hereby incorporated by reference.

U.S. Pat. No. 2,948,718 covers carbamazepine, a known anticonvulsant of structural formula

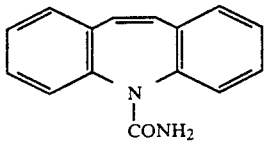

Carbamazepine has been reported to have antidepressant activity.

Arch Gen Psychiatry 47 287-8 (1990) discloses the use of progabide as an antidepressant. Progabide is There is no disclosure in the above references to make obvious the present invention of novel uses of compounds of U.S. Pat. No. 4,024,175 to treat depression.

Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Third Edition Revised) referred to as the DSM-III-R manual published by the American Psychiatric Association, 1987.

GABA is an inhibitory neurotransmitter within the central nervous system. Within the general context of inhibition, it seems likely that GABA-mimetics might decrease or inhibit cerebral function and might therefore slow function and decrease mood leading to depression.

The compound of the instant invention, gabapentin, may produce an anticonvulsant effect through the increase of newly created GABA at the synaptic junction. If gabapentin does indeed increase GABA levels or the effectiveness of GABA at the synaptic junction, then it could be classified as a GABA-mimetic and might decrease or inhibit cerebral function and might therefore slow function and decrease mood leading to depression.

The fact that a GABA agonist or GABA-mimetic, might work just the opposite way by increasing mood and thus, be an antidepressant, is a new concept, different from the prevailing opinion of GABA activity heretofore. Thus, gabapentin has now been found to have an antidepressant action in patients with major and minor forms of depression.

DETAILED DESCRIPTION

The present invention relates to novel methods of treating depression in a mammal in need of such treatment. The treatment comprises administering in unit dosage form an effective amount of a compound of formula

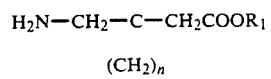

wherein $R_1$ is hydrogen or a lower alkyl and n is 4, 5, or 6 or a pharmaceutically acceptable salt thereof. The term lower alkyl includes straight or branched chain alkyl groups of up to eight carbon atoms.

Preferred compounds of formula I above include but are not limited to 1-aminomethyl-1-cyclohexane-acetic acid, ethyl 1-aminomethyl-1-cyclohexane-acetate, 1-aminomethyl-1-cycloheptane-acetic acid, 1-aminomethyl-1-cyclopentane-acetic acid, methyl 1-aminomethyl-1-cyclohexane-acetate, n-butyl 1-aminomethyl-1-cyclohexane-acetate, methyl 1-aminomethyl-1-cycloheptane-acetate, n-butyl 1-aminomethyl-1-cycloheptane-acetate, toluene sulfonate, 1-aminomethyl-1-cyclopentane-acetate, benzene-sulfonate, and n-butyl 1-aminomethyl-1-cyclopentane-acetate.

The most preferred compound is 1-aminomethyl-1-cyclohexane acetic acid (gabapentin).

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch, cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma, propylene glycol, glycerin; sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primary liquid composition. The most satisfactory compositions are those in which a much higher proportion of the active ingredient is present.

Routes of administration of the subject compound or its salts are oral or parenteral. For example, a useful intravenous dose is between 100 and 800 mg and a useful oral dosage is between 200 and 800 mg.

A unit dosage form of the instant invention may also comprise other compounds useful in the therapy of depression.

A typical dose is, for example, from 600 to 2400 mg per day given in three individual doses.

A skilled physician will be able to determine the appropriate situation in which subjects are susceptible to or at risk of minor or major depression for administration by methods of the present invention.

The advantages of using the compounds of formula I, especially gabapentin, in the instant invention include the relatively nontoxic nature of the compound, the ease of preparation, the fact that the compound is well tolerated, and the ease of IV administration of the drug. Further, the drug is not metabolized in the body.

The subjects as used herein are mammals, including humans.

The usefulness of compounds of formula I above and the salts thereof as agents for depression is demonstrated in the following case reports. Note that the patients undergoing treatment for epilepsy using gabapentin appear to be better dressed and to take better care of themselves, children are doing better in school; patients were more alert and some were more active.

| | | Beneficial Effect of Gabapentin | | |
|---|---|---|---|---|
| Patient | Age | Sex | Study Day | Effect |
| 1 | 51 | M | 78 | Less sluggish - able to perform better |
| 2 | 34 | F | 10 | Brighter and happier |
| 3 | 30 | F | 14 | Less depressed; more energy |
| 4 | 38 | M | 28 | More cheerful |
| 5 | 39 | F | 202 | Feels more positive about life |
| 6 | 25 | F | 28 | Much more alert and playful; increased activity, borders on hyperactivity Behavior at best since childhood |
| 7 | 27 | F | 29 | Improved mood |
| 8 | 32 | F | 119 | Better attitude |

Examples of formulations of the subject compound of salts thereof are illustrated by the following examples.

EXAMPLE 1

Injectables 1 mg to 100 mg/ml

Gabapentin
Water for Injection USP q.s.

The compound or a suitable salt thereof is dissolved in water and passed through a 0.2-micron filter. Aliquots of the filtered solution are added to ampoules or vials, sealed and sterilized.

EXAMPLE 2

Capsules 50 mg, 100 mg, 200 mg, 300 mg or 400 mg

Gabapentin, 250 g
Lactose USP, Anhydrous q.s. or 250 g
Sterotex Powder HM, 5 g

Combine the compound and the lactose in a tumble blend for two minutes, blend for one minute with the intensifier bar, and then tumble blend again for one minute. A portion of the blend is then mixed with the Sterotex Powder, passed through a 30 screen and added back to the remainder of the blend. The mixed ingredients are then blended for one minute, blended with the intensifier bar for 30 seconds, and tumble blended for an additional minute. The appropriately sized capsules are filled with 141 mg, 352.5 mg, or 705 mg of the blend, respectively, for the 50 mg, 125 mg, and 250 mg containing capsules.

EXAMPLE 3

Tablets 50 mg, 100 mg, 200 mg, 300 mg 400 mg, 500 mg or 600 mg

Gabapentin, 125 g
Corn Starch NF, 200 g
Cellulose, Microcrystalline, 46 g
Sterotex Powder HM, 4 g
Purified Water q.s. or 300 ml Combine the corn starch, the cellulose, and the compound together in a planetary mixer and mix for two minutes. Add the water to this combination and mix for one minute. The resulting mix is spread on trays and dried in a hot air oven at 50° C. until a moisture level of 1 to 2 percent is obtained. The dried mix is then milled with a Fitzmill through a RH2B screen, and added back to the milling mixture and the total blended for five minutes by drum rolling. Compressed tablets of 150 mg, 375 mg, and 750 mg, respectively, of the total mix are formed with appropriate sized punches the 50 mg, 125 mg, or 500 mg containing tablets.

I claim:

1. A method for treating depression which comprises administering a therapeutically effective amount of a compound of formula

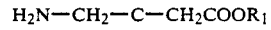

or a pharmaceutically acceptable salt thereof, wherein $R_1$ is hydrogen or a lower alkyl and n is 4, 5, or 6, in unit dosage form, to a mammal in need of said treatment.

2. A method according to claim 1 wherein n is 5 and $R_1$ is hydrogen, known as gabapentin, or a pharmaceutically acceptable salt thereof.

3. A method according to claim 1 wherein an individual dose of 5 mg to 50 mg parenterally or of 50 mg to 600 mg enterally of the compound or a pharmaceutically acceptable salt thereof is administered.

* * * * *

UNITED STATES PATENT AND TRADEMARK OFFICE
CERTIFICATE OF CORRECTION

PATENT NO. : 5,025,035
DATED : June 18, 1991
INVENTOR(S) : Jan D. Wallace

It is certified that error appears in the above—identified patent and that said Letters Patent is hereby corrected as shown below:

Column 4, line 50, please delete

" 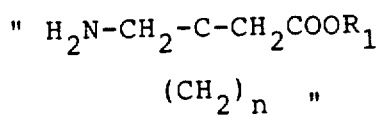   I and insert instead:

" 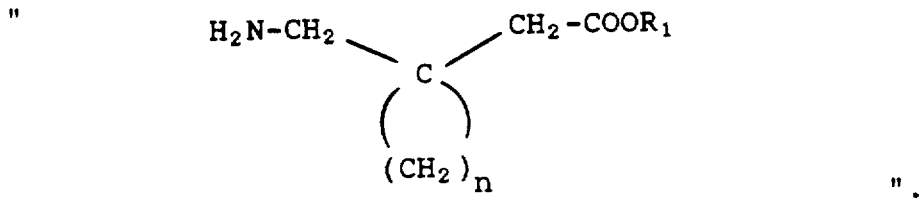

I
".

Signed and Sealed this

Fifth Day of January, 1993

Attest:

DOUGLAS B. COMER

*Attesting Officer*   *Acting Commissioner of Patents and Trademarks*